United States Patent [19]

Koepnick et al.

[11] 3,992,662

[45] Nov. 16, 1976

[54] LIQUID CONDUCTIVITY MEASURING DEVICE

[75] Inventors: Glenn Koepnick; Richard T. Balzen; Billy D. Etherton, all of Austin, Tex.

[73] Assignees: Billy D. Etherton; Eugene P. Ziner; William E. Berry; Russell J. Horn, all of Austin, Tex.

[22] Filed: Aug. 16, 1974

[21] Appl. No.: 498,192

[52] U.S. Cl. .............................. 324/30 R; 324/30 B
[51] Int. Cl.² ........................................ G01N 27/42
[58] Field of Search ............... 324/30 R, 30 B, 189, 324/30 A; 307/294

[56] References Cited
UNITED STATES PATENTS

| | | | |
|---|---|---|---|
| 3,047,797 | 7/1962 | Borsboom | 324/30 |
| 3,170,111 | 2/1965 | Case | 324/30 B |
| 3,393,360 | 7/1968 | Keating | 324/189 |
| 3,493,857 | 2/1970 | Silverman | 324/30 B |
| 3,657,640 | 4/1972 | Jelinek | 324/30 A |
| 3,701,006 | 10/1972 | Volkel | 324/30 B |
| 3,784,803 | 1/1974 | Brendle | 307/294 |

Primary Examiner—R. V. Rolinec
Assistant Examiner—Michael J. Tokar
Attorney, Agent, or Firm—Fidelman, Wolffe & Waldron

[57] ABSTRACT

A portable device for measuring the conductivity of a liquid between two probes spaced relative to each other along the lateral axis of a container. The gains of a plurality of operational amplifiers are varied for range, by conductivity and by temperature variations to provide a signal representative of the conductivity of the liquid. An oscillator using two operational amplifiers is used to drive the measuring amplifier.

12 Claims, 4 Drawing Figures

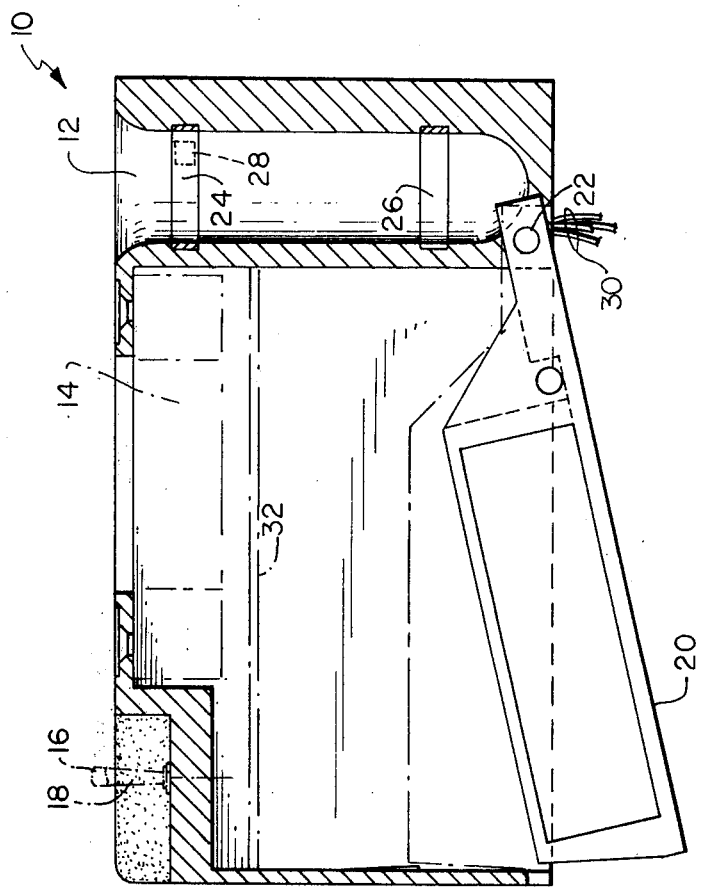
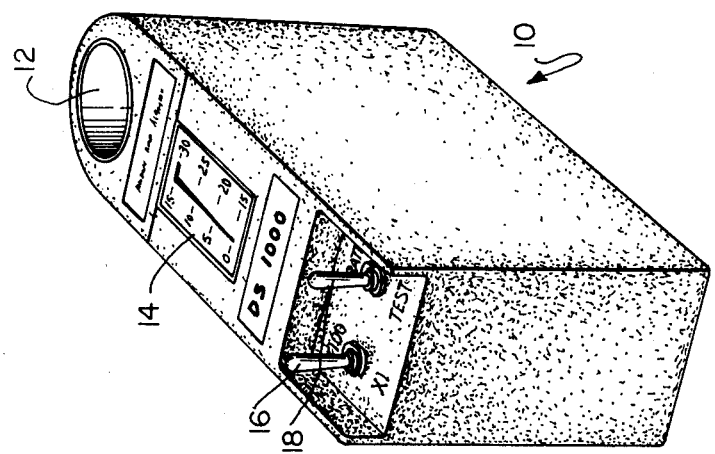

LIQUID CONDUCTIVITY MEASURING DEVICE

BACKGROUND OF THE INVENTION

1. Field of the Invention

The invention relates generally to apparatus for measuring the conductivity of liquids and more specifically to a portable solid state device for indicating the amount of contaminant salts in a sample of water.

2. Description of the Prior Art

In hospitals and laboratories, as well as in many maintenance and manufacturing situations, a need exists for a portable, easy to use device which measures with accuracy the amount of contaminated salts in samples of water. Prior devices have been developed which required skilled technicians to operate the equipment for any accuracy. Similarly, the equipment had to be continuously adjusted to assure its accuracy. Most devices of the prior art were somewhat large and bulky and thus inconvenient to carry and use except for isolated incidences and short distances. Thus a need exists for an instrument to measure the amount of contaminants in a water sample which may be easily carried, for example in the shirt pocket of the operator.

It is well known that the measure of the conductivity of water is proportional to the quantity of ionizable dissolved solids, which is in turn, proportional to the impurity content of the water. The measuring of contaminant content by conductivity is the most accurate measurement.

The prior art is generally measured the conductivity between two probes which are one leg of a bridge circuit. The bridge circuits of the prior art require the operation thereof by a skilled operator as well as numerous readjustments to keep the bridge in balance.

SUMMARY OF THE INVENTION

The present invention solves the problems of the prior art by using an oscillator powered by a DC source to produce an alternating current across two probes which are immersed in a liquid whose conductivity is to be measured. An operational amplifier having a plurality of resistors connected to its input is used to select the range of the signal to be applied to the probes. The conductivity of the liquid varies the gain of a second operational amplifier, which also includes a thermal responsive resistance mounted exterior to the solution on a probe which transmits the temperature of the liquid to the temperature responsive resistor. The output signal of the second operational amplifier is displayed on a meter which reads contaminants in parts per million. The electronics are contained on a printed circuit board, which is installed with dry celled batteries, meter and two switches into a molded housing which is less than 18 cubic inches in volume. The two probes are displaced relative to each other along the vertical axis of a container which is a unitary portion of the housing. The probes are an integral part of the housing and form a portion of the interior of said container.

The oscillator of the measurement circuit includes an operational amplifier operated without saturating having its input resistance vary periodically by a switch whose input is connected to the operational amplifier. The periodic switch is an operational amplifier having an RC circuit at its input. A pair of diodes are used to switch resistance in and out of the input circuit of the first operational amplifier to vary its input resistance or gain.

OBJECTS OF THE INVENTION

An object of the present invention is to provide a portable conductivity measuring device which fits in the shirt pocket of the operator.

Another object is to provide a conductivity measuring device which can be operated by persons other than skilled technicians.

A further object of the invention is to provide an inexpensive and accurate conductivity measuring device which requires no recalibration prior to use.

Still another object of the present invention is to provide a solid state circuitry for measuring the conductivity of liquids which is proportional to the contaminant salts contained in the liquid.

A still further object of the present invention is to provide an oscillator circuit using operational amplifiers which have a 50% duty cycle.

An even further object of the present invention is to provide a truly portable, easy to use, and accurate conductivity measuring device with a minimum number of parts and economically feasible for the general public.

Other objects, advantages and novel features of the present invention will become apparent from the following detailed description of the invention when considered in conjunction with the accompanying drawings.

BRIEF DESCRIPTION OF THE DRAWINGS

FIG. 1 is a perspective view of the preferred embodiment of the meter;

FIG. 2 is a cross-sectional view of the meter housing of FIG. 1;

BRIEF DESCRIPTION OF PREFERRED EMBODIMENTS

Figure 3:
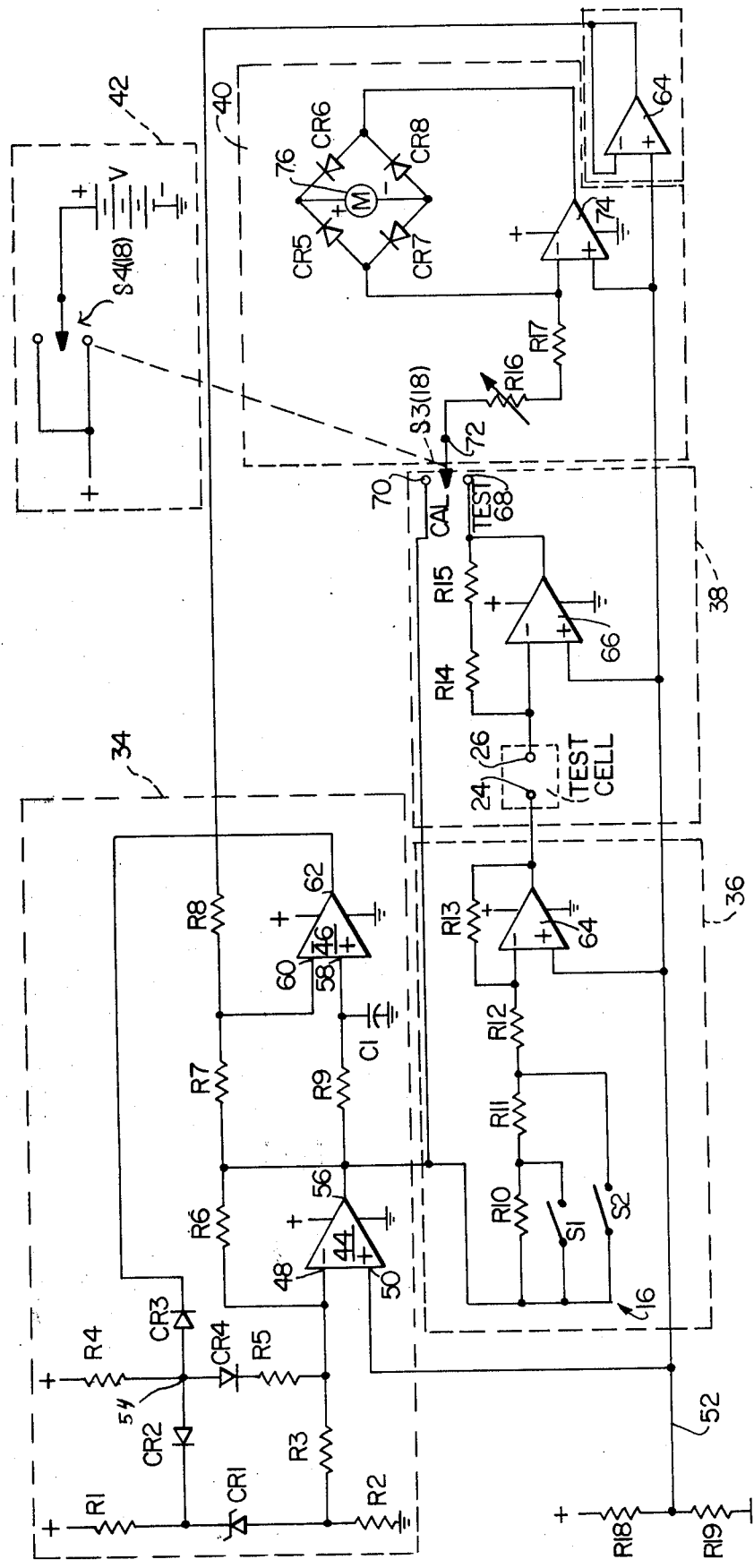
FIG. 3 is a schematic of the electronics of the preferred embodiment of the present invention.

FIG. 1 illustrates in perspective a preferred embodiment of the present meter housing 10 having a container 12 therein. A meter 14 (which illustrates, for example, contaminants in parts per million - PPM), a range switch 16 and a test/calibrate switch 18 are mounted to housing 10. Switches 16 and 18 are three positioned toggle switches. The overall volume occupied by housing 10 is less than 18 cubic inches and may have dimensions of, for example, approximately 4 inches long, approximately 2 inches high and approximately 1 inch wide. These suggested dimensions provide a housing which is easily carried in the shirt pocket of the operator.

A cross-section of the housing 10 is shown in FIG. 2 with all the elements not formed by molding shown in phantom. The housing 10 is made of molded plastic and included battery case 20 which is secured by hinges to the molded housing at 22. The battery case 20 generally carries, for example, a standard nine voltage battery as the DC power source for the electronic solid state circuit which will be explained in connection with the FIG. 3. The container 12 as shown is a unitary portion of said housing formed by the mold. Also forming a portion of the interior surface of container 12 are two electrodes 24 and 26. The electrodes are molded in place to form an integral part of the housing. The electrodes are displaced relative to each other along the vertical axis of the container 12. Mounted to the exterior of probe 24 is a temperature responsive element 28. The probe 24 acts as a temperature conductor of the temperature of the liquid to the temperature sensitive element 28. Though being shown as mounted on probe 24, temperature element 28 may also, if desired, be mounted to element 26. Four wires 30 are shown emerging from the bottom of the housing 10 which connect probes 24 and 26 and the temperature responsive element 28 to the electronic circuits mounted on the printed circuit board 32. The solid state circuits as shown in FIG. 3 fit under the meter 14 and above the battery casing 20 in the space provided. To increase the understanding of the present invention, only the circuit board 32 is shown in phantom in FIG. 2.

This schematic of FIG. 3 shows the circuitry of a preferred embodiment of the present invention including an oscillator 34, a range selection circuit 36, conductance sensor 38, a meter drive 40 and a power source 42. All plus signs shown on the circuitry of FIG. 3 indicate the plus side of the direct current source 42.

The oscillator 34 includes two operational amplifiers 44 and 46 connected in a closed loop configuration. As will be explained more fully, amplifier 44 is used as an amplifier and is operated within a range without saturation, whereas amplifier 46 is used as a bistable switch which oscillates between its high saturation voltage and its low saturation voltage. A reference voltage is provided by the series connection of resistors R1 and R2 and zener diode CR1. One input 48 of operational amplifier 44 is connected to the anode of zener diode CR1 by a resistor R3. The other input 50 of operational amplifier 44 is connected to a voltage divider comprising resistors R18 and R19. For the sake of clarity in explaining the present circuit, R18 will be considered equal to R19 so that the reference voltage on common line 52 will be considered the DC voltage V/2. Also connected to input 48 of operational amplifier 44 is a resistor R5. The resistor R5 is placed in and out of the input circuit of operational amplifier 44 by a switch comprising diode CR2, CR3, CR4 and resistor R4. The diodes are so arranged that when the CR3 is forward biased and conducting, the junction point 54 of the diodes is lower than the voltage at the cathodes of diodes CR2 and CR4. and thus they are reverse biased and nonconductive. Once CR3 is not forward biased and consequently nonconductive, the junction point 54 rises in voltage sufficiently that diode CR2 and CR4 are forward biased and thus conducting. When diode CR4 is forward biased, and thus conducting, the resistor R5 is placed in the input circuit of operational amplifier 44. Thus, it changes the voltage on input lead 48 of the operational amplifier. Diode CR2 is placed in the circuit to compensate for the voltage drop across the CR4.

If R1 and R2 are equal, the junction of R2 and R3 is at a potential lower than the V/2. As a matter of fact, the voltage at the junction of R2 and R3 is equal to V/2 - ½ voltage of the zener diode CR1. Thus, initially when the power is turned on and only R3 is the input resistance of 48, input 48 is low with respect to the input V/2 at input 50. The output 56 of amplifier 44 is fed back through resistor R6 such as to drive input 48 to be equal to input 50. It should be noted that output 56 is also the output of the oscillator circuit 34.

The operational amplifier 46 has inputs 58 and 60 and output 62. The output 62 is connected to diode CR3. The output 62 determines whether CR3 is forward or reverse biased and therefore controls the voltage at junction 54. As explained previously, the operational amplifier 46 operates as a bistable switch switching the output 62 between its high saturation voltage and its low saturation voltage. It should be noted that the low saturation voltage of operational amplifier 46 is greater than zero. When output 62 is at its high saturation voltage, CR3 is reverse biased not conducting and thus resistor R5 is in the input circuit of operational amplifier 44. When output 62 is in its low state, CR3 is forward biased, reducing the voltage at junction 54 and preventing CR4 from conducting and removing R5 from the input circuit of operational amplifier 44. Input 58 of operational amplifier 46 is connected to the output 56 of operational amplifier 44 through an RC circuit composing resistor R9 and capacitor C1. Since R9 comprises a charging and discharging path of capacitor C1, the charge and discharge time are equal. This point is very important since it produces the 50% duty cycle of oscillator 34. Input 60 of operational amplifier 46 is also connected to output 56 of operational amplifier 44 through a voltage divider having resistors R7 and R8. Resistor R8 is connected to line 52 through a buffer amplifier 64. The buffer amplifier is inserted to prevent errors or spurious voltages from the operational amplifiers of the range select, conductance sensor, and the meter drive circuit from being transmitted to the oscillator circuit 34. By making R7 equal to R8, pin 60 oscillates about the voltage V/2. The swing of the oscillation is controlled by the output 56 of operational amplifier 44. The swing of output 56 is determined by the gain of operational amplifier 44 which is determined by the voltage drop across the zener diode CR1.

Figure 4:
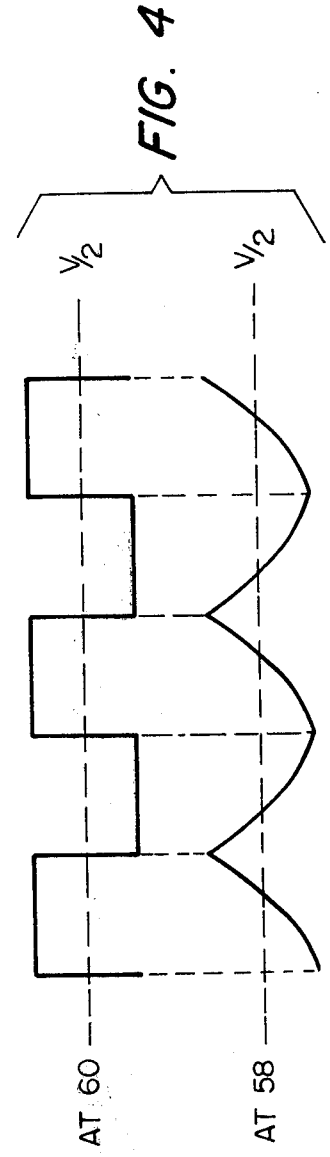
FIG. 4 is a series of graphs of the voltages at inputs 58 and 60 of operational amplifier 46.

As explained earlier, when the power is first turned on, input 48 of operational amplifier 44 is lower than input 50 and thus output 56 is positive. When output 56 is positive, input 60 is greater than input 58 of operational amplifier 46 and output 62 is low. With 62 low, resistor R5 is prevented from being part of the input of operational amplifier 44. The input 58 on operational amplifier 46 is charged to the voltage at input 60. The voltage at inputs 50 and 68 are shown in FIG. 4 as oscillating about the voltage V/2. Once the input at 58 approaches very closely the value at input 60, the operational amplifier 46 transfers to its high saturation output voltage. When this occurs, diode CR3 is reverse biased raising the potential at junction 54 and forward biasing diode CR2 and CR4. The forward biasing of resistor CR4 places R5 on the input 48 of operational amplifier 44. By changing the loading conditions on input 48, the operational amplifier 44 is switched to its low state, allowing capacitor C1 to discharge through R9. Once capacitor C1 is completely discharged, operational amplifier 46 is again unbalanced causing operational amplifier 46 to switch output 62 to a low state. This forward biases diode CR3 and removes R5 from the input 48 of operational amplifier 44 and starts the oscillation cycle all over again, charging capacitor C1.

The preferred embodiment of operational amplifier 34 provides a solid state 50% duty cycle oscillator using two operational amplifiers, one in the amplifying mode and the other in the switching mode.

The output of oscillator 34 is an alternating signal which is transmitted to probe 24 through a range selection circuit 36. The range selection switch 36 includes an operational amplifier 64 having one input connected to bias voltage line 52 and the other input connected through a plurality of resistors to the output of oscillators circuit 34. A feedback resistor R13 is connected between the output and input of the operational amplifier 64. The input resistance of operational amplifiers 64 is composed of three series resistors R10, R11 and R12. Schematically connected across resistor R10 is switch S1 and connected across resistors R10 and R11 is switch S2. Switches S1 and S2 are schematically represented by two of the positions of toggle switch 16 illustrated in FIG. 1. When switches 16 is in its first position, switches S1 and S2 are open so that the input resistance amplifier 64 is the sum of the three resistors R10, R11 and R12. When switch 16 is in a second position, schematic switch S1 removes R10 from the input circuit. When switch 16 is in its third position, switch S2 is closed, removing resistor R10 and R11 from the input circuit of operational amplifier 64. By changing the input resistance of operational amplifier 64, the gain of the amplifier is therefore varied. Resistors R10, R11 and R12 may be chosen such that when switch S1 is closed, the gain of the amplifiers is ten times that when the switches S1 and S2 are open. Similarly, when S2 is closed, the gain is ten times that of when S1 is closed or 100 times that of when switches S1 and S2 are open. These gain factors are but by way of example and the resistors R10, R11 and R12 may be selected to give any multiple of range desired.

The alternating signal from range circuit 36 is applied to the liquid in container 12 across probes 24 and 26. It should be noted that the output of range 36 is shown as being attached to probe 24 but may be attached to probe 26 if desired, and thus the probes 24 and 26 are interchangeable in the schematic circuit. The conductivity of the liquid between probes 24 and 26 vary the input resistance of operational amplifier 66 of the conductance sensor circuit 38. Operational amplifier 66 has feedback resistors R14 and R15. The resistor R15 is a thermistor which is the temperature sensitive element 28 illustrated in FIG. 2. By placing resistor R15 in series with the reference resistor R14, the gain of the amplifier 66 is linearly adjusted for variations in temperature.

The output of the operational amplifier 66 is connected to the meter drive circuit through a switch S3. Switch S3 has two inputs 68 and 70 and an output 72. Switch S3 is ganged to a second switch S4 which is connected to the power source circuit 42. Switch S3 and S4 are three position toggles which are controlled by switch 18 illustrated in FIG. 1. When toggle switch 18 is in the center position, the battery of the power source circuit 42 is disconnected from the circuit and thus no energy is drained therefrom, prolonging the life of the battery. When switch 18 is moved to a lower position, output 72 is connected to input 68, the output of the operational amplifier 66 is transmitted to the meter circuit 40. When the toggle switch 18 is in its upper position, the output 72 is connected to the input 70. The range circuit 36 and the conductance sensor 38 are bypassed and the oscillator drives the meter circuit 40 directly. This may be used to indicate that the battery is operative as well as to calibrate the meter drive circuit 40.

The meter drive circuit 40 includes a variable resistor R16 and a fixed resistor R17 connected to an operational amplifier 74. The variable R16 provides an adjustment for the meter drive circuit. A direct current meter 76 is across the center of a diode bridge including diode CR5, CR6, CR7 and CR8. The input of the bridge is connected in the feedback circuit of operational amplifier 74.

The solid state circuitry of the preferred embodiment illustrated in FIG. 3 provides an accurate and economical liquid conductivity measuring device which reduces the amount of calibration needed and increases accuracy and range. The small volume of casing 10 in combination with the solid state circuitry provides an inexpensive and totally portable apparatus for measuring the amount of contaminant salts present in a water sample.

From the preceding description of the preferred embodiments, it is evident that the objects of the invention are attained. Although the invention has been described and illustrated in detail, it is to be understood that the same is by way of illustration and example only and is not to be taken by way of limitation. The selection of the various values of resistance are but by way of example and were picked for clarity of explanation. The spirit and scope of the invention are limited only by the terms of the appended claims.

What is claimed is:
1. An apparatus for measuring the conductivity of liquids comprising:
   means for producing an oscillating output signal;
   range means, connected to the output of said oscillator means, for varying the amplitude of said output signal of said oscillator means, said range means includes a range operational amplifier, a plurality of resistors connected between the output of said oscillator means and the input of said range amplifier and a plurality of switches connected across said resistors so that selected resistors may be added or removed from the input resistance of said range amplifier and said plurality of resistors is three and said plurality of switches is two, one switch is connected in parallel with a first resistor and the other switch is connected in parallel with said first resistor and a second resistor;
   two probes to be placed in contact with the liquid, whose conductivity is to be measured, one of said probes being connected to the output of said range means;
   amplifier means, connected to the other of said probes, whose gain varies in response to the conductivity of said liquid; and
   an indicator means connected to the output of said amplifier means for indicating said liquid's conductivity.
2. An apparatus for measuring the conductivity of liquids comprising:
   means for producing an oscillating output signal including a first and second operational amplifier, said first amplifier's output being connected to an input of said second amplifier through an RC circuit, and gain means connected to both of said amplifiers for varying the gain of said first amplifier in response to the output of said second amplifier, the output of said first amplifier is the output of said oscillator means;
   range means connected to the output of said oscillator means for varying the amplitude of said output signal of said oscillator means;
   measuring means comprised of two probes to be placed in contact with the liquid, whose conductivity is to be measured, one of said probes being connected to the output of said range means and including a temperature responsive means connected to said measuring means and mounted directly to one of said probes exterior to the inner surface of said container means and within said housing, said one of said probes transmitting the temperature of a liquid in said container means to said temperature responsive means;

amplifier means, connected to the other of said probes, whose gain varies in response to the conductivity of said liquid; and an indicator means connected to the output of said amplifier means for indicating said liquid's conductivity.

3. An apparatus for measuring the conductivity of liquid comprising:

means for producing an oscillating output signal;

range means connected to the output of said oscillator means for varying the amplitude of said output signal of said oscillator means, said range means includes a range operational amplifier, a plurality of resistors connected in series between the output of said oscillator means and the input of said range amplifier and a plurality of switches connected across said resistors so that selected resistors may be added or removed from the input resistance of said range amplifier;

two probes to be placed in contact with the liquid, whose conductivity is to be measured, one of said probes being connected to the output of said range means;

amplifier means, connected to the other of said probes, whose gain varies in response to the conductivity of said liquid; and an indicator means connected to the output of said amplifier means for indicating said liquid's conductivity.

4. An apparatus for measuring the conductivity of liquids comprising:

means for producing an oscillating output signal;

range means connected to the output of said oscillator means for varying the amplitude of said output signal of said oscillator means;

two probes to be placed in contact with the liquid, whose conductivity is to be measured, one of said probes being connected to the output of said range means;

amplifier means, connected to the other of said probes, whose gain varies in response to the conductivity of said liquid;

an indicator means connected to the output of said amplifier means for indicating said liquid's conductivity; and first switch means connected to said indicator means, said first switch means selectively interconnecting said indicator means to one member of the group consisting of said oscillator means for calibration and said amplifier means for reading the conductivity of said liquid on said indicator means, and an open circuit.

5. The apparatus of claim 4 including power switch means connecting said power source to the elements of the apparatus, said power switch means and said first switch means being three position toggle switches and being mechanically ganged so that the power source is connected to the elements of the apparatus by said power switch when said first switch means if selectively positioned either for calibrating or reading conductivity and said power switch means is open when said first switch means is open.

6. An apparatus for measuring the conductivity of liquids comprising:

means for producing an oscillating output signal;

range means connected to the output of said oscillator means for varying the amplitude of said output signal of said oscillator means;

a container having an opening in the top thereof for holding the liquid whose conductivity is to be measured;

two probes displaced along the vertical axis of said container relative to each other one of said probes being connected to the output of said range means;

amplifier means connected to the other of said probes;

means responsive to the temperature of said liquid connected to said amplifier means and mounted directly to one of said probes, said probe transferring the temperature of said liquid to said temperature responsive means;

the gain of said amplifier means varies in response to the conductivity of said liquid and said temperature responsive means; and an indicator means connected to the output of said amplifier means for indicating said liquid's conductivity.

7. An apparatus for measuring the conductivity of liquids comprising:

means for producing an oscillating output signal including a first and second operational amplifier, said first amplifier's output being connected to an input of said second amplifier through an RC circuit, and gain means connected to both of said amplifiers for varying the gain of said first amplifier in response to the output of said second amplifier, the output of said first amplifier is the output of said oscillator means;

range means connected to the output of said oscillator means for varying the amplitude of said output signal of said oscillator means;

two probes to be placed in contact with the liquid, whose conductivity is to be measured, one of said probes being connected to the output of said range means;

amplifier means, connected to the other of said probes, whose gain varies in response to the conductivity of said liquid; and an indicator means connected to the output of said amplifier means for indicating said liquid's conductivity.

8. The apparatus of claim 7 wherein said second amplifier operates at either its upper or lower saturation states and said RC circuit cause said second amplifier to switch between its saturation states periodically.

9. The apparatus of claim 7 wherein said gain means includes a pair of diodes and a resistor, one diode is connected to a common junction and the output of said second amplifier and the other diode is connected in series with said resistor between said common junction and an input to said first amplifier so that only one of said diodes at a time is conducting and said resistor varies the input resistance of said first amplifier.

10. The apparatus of claim 8 wherein said periodic switching has a 50% duty cycle and said first amplifier operates without saturating.

11. A device for indicating conductivity of a liquid comprising:

a housing;

a container means being an integrally formed portion of said housing for receiving said liquid, said container means having an opening in its top for entry of said liquid;

a pair of probes in said container means displaced from each other along the vertical axis of said container means and forming a portion of the interior surface of said container means;

means in said housing for measuring the conductivity of a liquid contacting both probes and providing a signal representative of said conductivity; and an indicator in said housing and connected to said means measuring for displaying the conductivity of said liquid.

12. The device of claim 11 wherein said housing is less than 18 cubic inches in volume and said device includes a power source within said housing.

* * * * *